US012694274B2

(12) United States Patent
Farris et al.

(10) Patent No.: US 12,694,274 B2
(45) Date of Patent: Jul. 28, 2026

(54) SYSTEMS AND METHODS FOR DETECTING CRISPR-MEDIATED RESIDUES WITHIN METHYLATED PATTERNS OF GENOME USING A CONVOLUTIONAL NEURAL NETWORK

(71) Applicant: MITRE Corporation, McLean, VA (US)

(72) Inventors: Heath Farris, McLean, VA (US); Tyrone V. Patterson, III, McLean, VA (US); Eliza M. Mace, McLean, VA (US); Patrick Hinson, McLean, VA (US); Kris Rosfjord, McLean, VA (US)

(73) Assignee: MITRE Corporation, McLean, VA (US)

( * ) Notice: Subject to any disclaimer, the term of this patent is extended or adjusted under 35 U.S.C. 154(b) by 614 days.

(21) Appl. No.: 18/199,796

(22) Filed: May 19, 2023

(65) Prior Publication Data

US 2024/0386285 A1     Nov. 21, 2024

(51) Int. Cl.
| | |
|---|---|
| *G06N 3/04* | (2023.01) |
| *G06N 3/0464* | (2023.01) |
| *G06N 3/088* | (2023.01) |
| *G06T 11/00* | (2006.01) |
| *G16B 20/20* | (2019.01) |

(52) U.S. Cl.
CPC ........... *G06N 3/0464* (2023.01); *G06N 3/088* (2013.01); *G06T 11/00* (2013.01); *G16B 20/20* (2019.02)

(58) Field of Classification Search
CPC .............................. G06N 3/0464; G16B 20/20
See application file for complete search history.

(56) References Cited

U.S. PATENT DOCUMENTS

| | | | |
|---|---|---|---|
| 2021/0395799 A1* | 12/2021 | Dobosy .................. | C12N 15/11 |
| 2022/0358697 A1* | 11/2022 | Selim .................... | G06N 3/0464 |
| 2024/0203530 A1* | 6/2024 | Lo .......................... | G06N 20/00 |
| 2025/0037801 A1* | 1/2025 | Sun ......................... | G16B 40/20 |

OTHER PUBLICATIONS

Xue, Li, et al. "Prediction of CRISPR sgRNA activity using a deep convolutional neural network." Journal of chemical information and modeling 59.1 (2018): 615-624. (Year: 2018).*

(Continued)

*Primary Examiner* — Hal Schnee
(74) *Attorney, Agent, or Firm* — Jones Day

(57) ABSTRACT

A system, method, and computer-readable medium for detecting a CRISPR-edited genome are disclosed. Certain embodiments of the system may include one or more processors configured to receive sequence data of a genome; generate an image representation of the sequenced data, the image being a plot of methylation variations as a function of methylation locations in the genome; apply the generated image representation to a trained convoluted neural network (CNN); generate, using the CNN, a score indicative of a probability that the genome was CRISPR-edited; and determine, based on the score, whether the genome contains a CRISPR-edited methylation region. A corresponding method and computer-readable medium are also provided.

20 Claims, 9 Drawing Sheets

100 Process for Detecting
CRISPR-mediated Methylome
Residues

Begin

Receive sequence data of a genome suspected of having a CRISPR edit — 102

Generate an image representation of the sequence data — 104

— 106

Convolve pixel data of the image representation to create feature maps — 108

Downsample feature maps via pooling layer — 110

Score image representation using neural network — 112

Determine if the genome has a CRISPR edit — 114

End

(56)     References Cited

OTHER PUBLICATIONS

Wang, Jiandong, et al. "EditPredict: Prediction of RNA editable sites with convolutional neural network." Genomics 113.6 (2021): 3864-3871. (Year: 2021).*

Ouyang, Zhangyi, et al. "Accurate identification of RNA editing sites from primitive sequence with deep neural networks." Scientific reports 8.1 (2018): 6005. (Year: 2018).*

Somodevilla, Mario Rossainz L., and M. Rossainz. "DNA sequence recognition using image representation." Res Comput Sci 148 (2019): 105-114. (Year: 2019).*

Muneeb, Muhammad, Samuel F. Feng, and Andreas Henschel. "Can we convert genotype sequences into images for cases/ controls classification?." Frontiers in Bioinformatics 2 (2022): 914435. (Year: 2022).*

* cited by examiner

100 Process for Detecting
CRISPR-mediated Methylome
Residues

200 Process for Training a Convolution Neural Network to Detect CRISPR-mediated Methylome Residues 300 Example Image Representation of WGBS Data 304 Close-up of Plot Segment Emphasizing Distinctive Pattern Indicative of CRISPR-Edit Plot of Relative Methylation Along Chromosome 300 Example Image Representation of WGBS Data 306 Close-up of Plot Segment Emphasizing Stratification of Epigenetic Variance Plot of Relative Methylation Along Chromosome

302

● = methylation at one CpG location

Methylation

Chromosome Location

400 Generation of Additional Image Representations for Training

500 Process for Detecting CRISPR-
mediated Methylome Residues
Using A CNN and Another Network 600 Example User Interface that Indicates CRISPR Edits 700 Comparison Chart of Various CNN-Model Configurations
Showing Loss as a Function of Multiple Hyperparameters

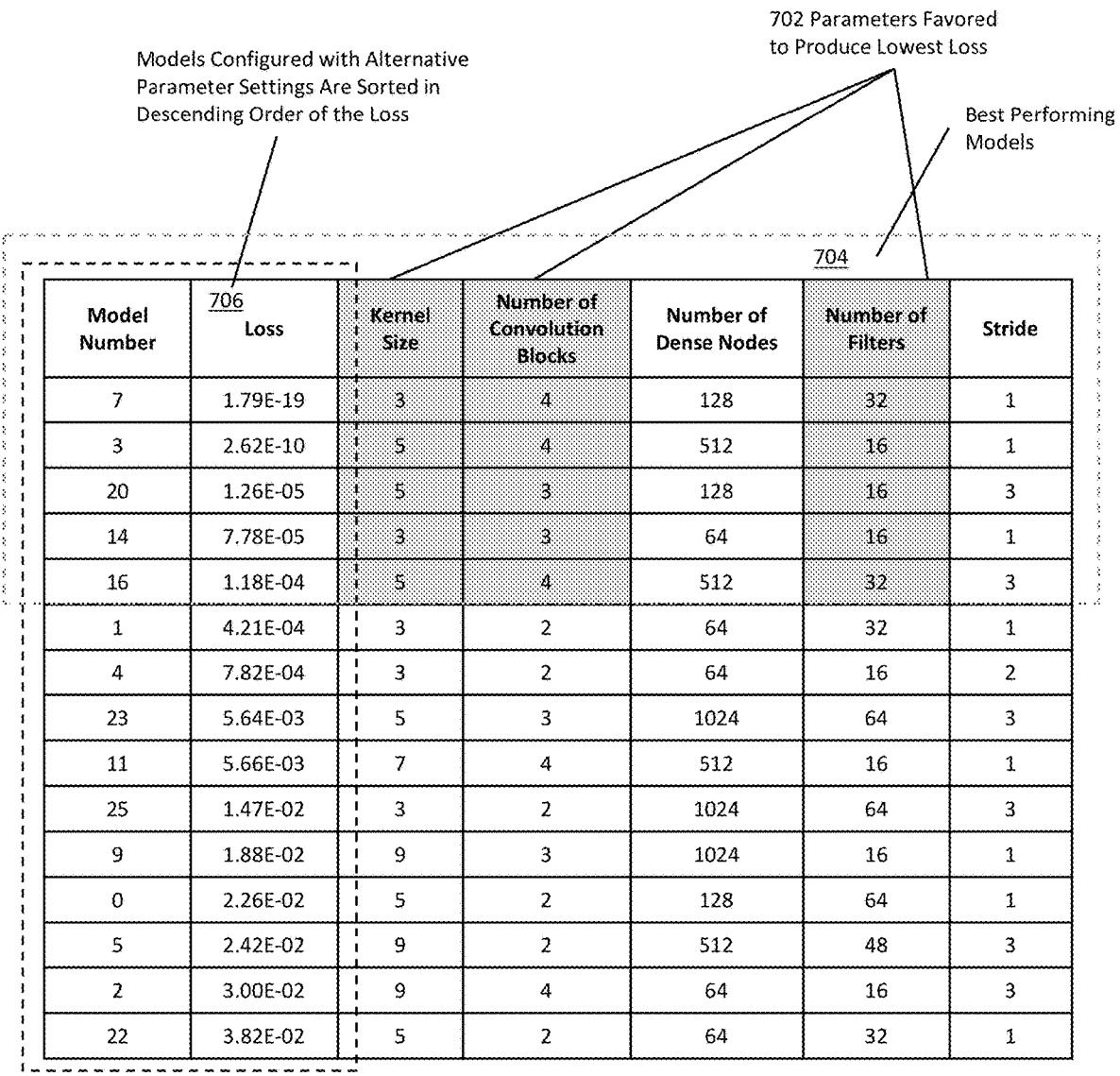

702 Parameters Favored
to Produce Lowest Loss

Models Configured with Alternative
Parameter Settings Are Sorted in
Descending Order of the Loss Best Performing
Models

704

| Model Number | 706 Loss | Kernel Size | Number of Convolution Blocks | Number of Dense Nodes | Number of Filters | Stride |
|---|---|---|---|---|---|---|
| 7 | 1.79E-19 | 3 | 4 | 128 | 32 | 1 |
| 3 | 2.62E-10 | 5 | 4 | 512 | 16 | 1 |
| 20 | 1.26E-05 | 5 | 3 | 128 | 16 | 3 |
| 14 | 7.78E-05 | 3 | 3 | 64 | 16 | 1 |
| 16 | 1.18E-04 | 5 | 4 | 512 | 32 | 3 |
| 1 | 4.21E-04 | 3 | 2 | 64 | 32 | 1 |
| 4 | 7.82E-04 | 3 | 2 | 64 | 16 | 2 |
| 23 | 5.64E-03 | 5 | 3 | 1024 | 64 | 3 |
| 11 | 5.66E-03 | 7 | 4 | 512 | 16 | 1 |
| 25 | 1.47E-02 | 3 | 2 | 1024 | 64 | 3 |
| 9 | 1.88E-02 | 9 | 3 | 1024 | 16 | 1 |
| 0 | 2.26E-02 | 5 | 2 | 128 | 64 | 1 |
| 5 | 2.42E-02 | 9 | 2 | 512 | 48 | 3 |
| 2 | 3.00E-02 | 9 | 4 | 64 | 16 | 3 |
| 22 | 3.82E-02 | 5 | 2 | 64 | 32 | 1 |

FIG. 7

800 Model Prediction Testing

Predicted Sites of CRISPR-Edits Ranked According to Probability

804 Probability Outputs for Various Models Are Compared

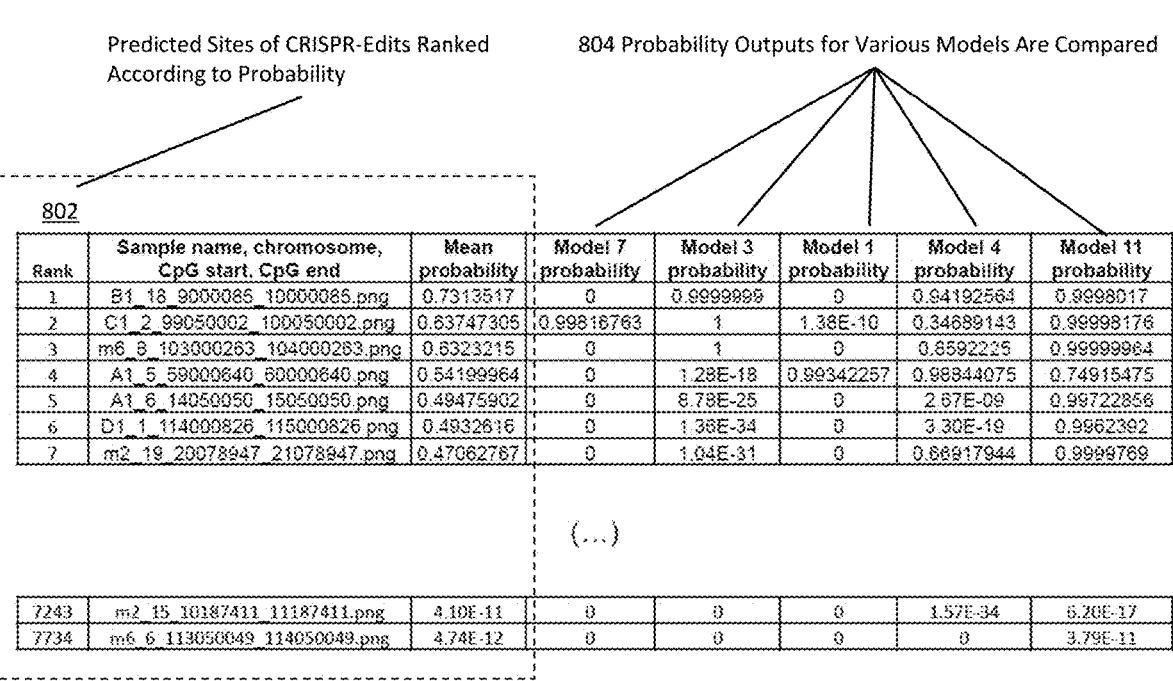

802

| Rank | Sample name, chromosome, CpG start, CpG end | Mean probability | Model 7 probability | Model 3 probability | Model 1 probability | Model 4 probability | Model 11 probability |
|---|---|---|---|---|---|---|---|
| 1 | B1_16_9000085_10000085.png | 0.7313517 | 0 | 0.9999999 | 0 | 0.94192564 | 0.9998017 |
| 2 | C1_2_99050002_100050002.png | 0.63747305 | 0.99816763 | 1 | 1.36E-10 | 0.34689143 | 0.39998176 |
| 3 | m6_8_103000263_104000263.png | 0.6323215 | 0 | 1 | 0 | 0.8592226 | 0.99999964 |
| 4 | A1_5_59000640_60000640.png | 0.54199964 | 0 | 1.28E-18 | 0.99342257 | 0.98844075 | 0.74915475 |
| 5 | A1_6_14050050_15050050.png | 0.49475902 | 0 | 8.78E-25 | 0 | 2.67E-09 | 0.99722856 |
| 6 | D1_1_114000826_115000826.png | 0.4932616 | 0 | 1.36E-34 | 0 | 3.30E-19 | 0.9962392 |
| 7 | m2_19_20078947_21078947.png | 0.47062767 | 0 | 1.04E-31 | 0 | 0.68917944 | 0.9999769 |

(...)

| 7243 | m2_15_10187411_11187411.png | 4.10E-11 | 0 | 0 | 0 | 1.57E-34 | 6.20E-17 |
| 7734 | m6_6_113050049_114050049.png | 4.74E-12 | 0 | 0 | 0 | 0 | 3.79E-11 |

FIG. 8

SYSTEMS AND METHODS FOR DETECTING CRISPR-MEDIATED RESIDUES WITHIN METHYLATED PATTERNS OF GENOME USING A CONVOLUTIONAL NEURAL NETWORK

TECHNICAL FIELD

The present application pertains to systems and methods for training and detecting CRISPR-mediated alterations to methylome regions. More specifically, the present application pertains to systems and methods for training and detecting CRISPR-mediated alterations to cytosine-phosphate-guanine (CpG) island (CGI) and sub-CGI locations using convolutional neural networks.

BACKGROUND

A number of gene editing methods exist that provide techniques to treat genetic, viral and bacterial diseases. CRISPR (Clustered Regularly Interspaced Short Palindromic Repeats) gene editing is a powerful tool for generating genomic edits with high precision and efficiency. CRISPR functions by creating a DNA double-strand break ("DSB") at a target site. After the DSB is made, the cell may use one of several processes, such as non-homologous end joining (NHEJ), to repair the DSB. During NHEJ, nucleotides may be added or removed by the cell, which results in a sequence that is different from the original targeted sequence. Another possibility is that the cell may repair a DSB by homology-directed repair ("HDR") or homologous recombination ("HR") mechanisms, which utilize an endogenous or exogenous donor template with homology to each end of the DSB to direct repair of the break.

A vertebrate genome has regions with a high number of CpG dinucleotides known as CpG islands ("CGIs"). In mammals, CGIs are targets of methylation (i.e., a chemical modification of DNA and other molecules that may be retained as cells divide to make more cells). The methylation patterns across the genome are reset and reestablished during embryogenesis. CGIs are typically located in gene regulatory elements, such as promoters and enhancers. The methylation of CGIs plays a role in whether a gene is active or inactive.

Multiple factors can influence the methylation state of the genome. For example, CRISPR can alter the methylation patterns of CGIs within the region of the genome being targeted. Specifically, when CRISPR targets a CGI region, the CRISPR-generated edits can result in an increase in methylation of the CGIs. Thus, there is a need for methods for detecting changes in methylation as a result of CRISPR-mediated genome editing.

SUMMARY

According to certain embodiments, a system for detecting a CRISPR-edited genome is disclosed. The system is characterized by one or more processors configured to receive sequence data of a genome; generate an image representation of the sequenced data, the image being a plot of methylation variations as a function of methylation locations in the genome; apply the generated image representation to a trained convoluted neural network (CNN); generate, using the CNN, a score indicative of a probability that the genome was CRISPR-edited; and determine, based on the score, whether the genome contains a CRISPR-edited methylation region. According to certain embodiments, the CNN of the system was trained using: (1) a training image representing sequenced data of a CRISPR-edited genome, and (2) an additional training image generated based on the training image. According to certain embodiments of the system, the additional training image is generated by (1) duplicating the training image, and (2) replicating a part of the training image corresponding to a CRISPR-edited methylation region of the CRISPR-edited genome to a part of the duplicated training image corresponding to a different methylation region.

According to certain embodiments, the system is further characterized by sequenced data consisting of whole-genome bisulfite sequencing (WGBS) data and image representations of sequenced data consisting of Manhattan plots. The CNN of the system includes convolution layers and a pooling layer and, after the system determines that the genome contains a CRISPR-edited methylation site, the image representation of the sequenced data is used to further train the CNN. The determining may include determining a methylation location of the CRISPR edit. Furthermore, according to certain embodiments, one or more processors may be further configured to determine, using a long short term memory network (LSTM), whether the genome likely contains a CRISPR-edited methylation site, wherein the determining includes weighing the generated score and results from the LSTM to determine whether the genome contains a CRISPR edit.

According to certain embodiments, a method for detecting a CRISPR-edited genome is disclosed. The method is characterized by receiving sequence data of a genome; generating an image representation of the sequenced data, the image being a plot of methylation variations as a function of methylation locations in the genome; applying the generated image representation to a trained CNN; generating, using the CNN, a score indicative of a probability that the genome was CRISPR-edited; and determining, based on the score, whether the genome contains a CRISPR-edited methylation region. According to certain embodiments, the CNN of the method was trained using: (1) a training image representing sequenced data of a CRISPR-edited genome, and (2) an additional training image generated based on the training image. According to certain embodiments of the method, the additional training image is generated by (1) duplicating the training image, and (2) replicating a part of the training image corresponding to a CRISPR-edited methylation region of the CRISPR-edited genome to a part of the duplicated training image corresponding to a different methylation region.

According to certain embodiments, the method is further characterized by having sequenced data consisting of WGBS data and image representations of sequenced data consisting of Manhattan plots. The CNN of the method includes convolution layers and a pooling layer and after determining that the genome contains a CRISPR-edited methylation site, the method uses the image representation of the sequenced data to further train the CNN. The process of determining that the genome contains a CRISPR-edited methylation site may include determining a methylation location of the CRISPR edit. Additionally, the process of determining whether the genome likely contains a CRISPR-edited methylation site may further include weighing a generated score and results from an LSTM to determine whether the genome contains a CRISPR edit.

According to certain embodiments, the present disclosure describes a non-transitory computer-readable storage medium storing instructions that when executed by a computer cause the computer to perform a method for detecting a CRISPR-edited genome. The method is characterized receiving sequence data of a genome; generating an image representation of the sequenced data, the image being a plot of methylation variations as a function of methylation locations in the genome; applying the generated image representation to a trained CNN; generating, using the CNN, a score indicative of a probability that the genome was CRISPR-edited; and determining, based on the score, whether the genome contains a CRISPR-edited methylation region. According to certain embodiments, the CNN of the method was trained using: (1) a training image representing sequenced data of a CRISPR-edited genome, and (2) an additional training image generated based on the training image. According to certain embodiments of the method, this additional training image is generated by (1) duplicating the training image, and (2) replicating a part of the training image corresponding to a CRISPR-edited methylation region of the CRISPR-edited genome to a part of the duplicated training image corresponding to a different methylation region.

According to certain embodiments, the method includes having sequenced data consisting of WGBS data and image representations of sequenced data consisting of Manhattan plots. The CNN of the method includes convolution layers and a pooling layer and, after determining that the genome contains a CRISPR-edited methylation site, the method uses the image representation of the sequenced data to further train the CNN. The process of determining whether the genome contains a CRISPR-edited methylation site may also include determining a methylation location of the CRISPR edit.

BRIEF DESCRIPTION OF THE DRAWINGS

Embodiments of the present disclosure will be described with reference to the accompanying drawings, in which:

FIG. 7 illustrates an example of a table used to compare and competitively select for combinations of CNN hyperparameters that minimize the loss of their corresponding models.

FIG. 8 illustrates an example of a table used to rank the relative likelihoods that a CRISPR-edit exists at various CpG sites by taking into account the predictions made by multiple CNN models and calculating an overall mean probability.

DETAILED DESCRIPTION

Figure 1:
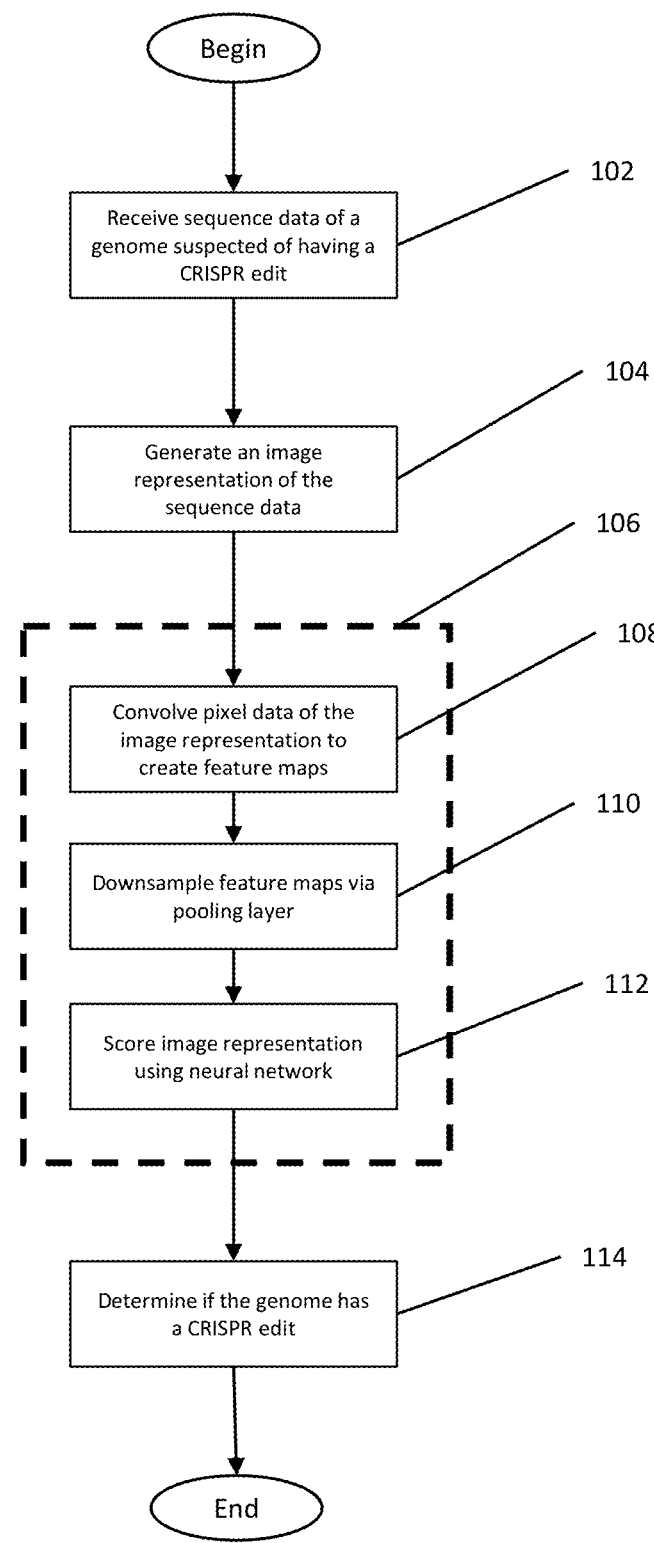
FIG. 1 is a flow diagram of a process for detecting CRISPR-mediated methylome residues using a convolution neural network (CNN), in accordance with some embodiments.

The field of epigenetics pertains to the study of changes to a genome that do not involve changes to its nucleotide sequence and their phenotypic effects. DNA methylation and demethylation are the primary mechanisms involved in conferring epigenetic change and therefore heavily control the expression of all genes that comprise a genome. The expression of physical traits in animals is highly dependent on the regional levels of methylation enrichment occurring at the genes that encode for those traits. Currently, there is no dedicated, reliable, universal tool available with which to detect and track changes to methylation patterns incurred during the use of CRISPR technology to edit a genome. This underscores an inherent risk and potential shortcoming in the mass adoption of CRISPR techniques—an inability to anticipate the actual, phenotypic outcome of a particular edit.

Cytosine-phosphate-guanine (CpG) sites are regions of DNA where a cytosine nucleotide is followed by a guanine nucleotide in a linear sequence of bases and are often targets of important epigenetic activity. CpG sites occur with high frequency in genomic regions called CpG islands (CGIs). CGIs are typically located in gene promoter regions, gene enhancer regions, or within genes themselves and may play an important role in the biological regulation of gene expression. CGIs are commonly maintained in a hypomethylated state. Inducing changes to these preserved methylation patterns within the epigenome can have transgenerational effects, with progeny exhibiting the same modifications created within the parental strains. Unintended deregulation of regulatory elements due to the collateral effects of CRISPR editing could likely have unpredictable consequences for the cell and hence the organism. In particular, CRISPR edits leveraging homology directed repair (HDR) mechanisms in combination with donor homology arms localized around CGIs (and even sub-CGI CpG sites) induce modifications of the methylation patterns occurring at these genomic sections, resulting in distinctively augmented and persistent methylation within the recombinant region.

The following provides a disclosure of systems and methods for detecting genomic scars inflicted by application of CRISPR (i.e., in which the original methylation states of cytosine bases become permanently reversed). The process involves training a convolutional neural network to recognize patterns occurring within image representations of genomic sequence data, such as a Manhattan plot of raw whole genome bisulfite sequencing (WGBS) data. The disclosed embodiments allow for fast, precise, and reliable examination and diagnosis of a CRISPR-modified genomic sample by pinpointing an affected particular loci or CpG site.

The detection process is generalizable to a wide-range of organisms. Across different mammalian systems, CpG locations are available for targeted methylation, and many species have been genetically modified using CRISPR and CRISPR-derived technologies. Additionally, epigenetic residues imparted by CRISPR-mediated incorporation of donor DNA using HDR mechanisms are conserved among mammalian systems, providing further support for the broad application of this detection methodology. Mammalian applications include human cell cultures, non-human primates, rats, elephants, goats, pigs, mice, and cows.

FIG. 1 illustrates a flow diagram of a process 100 for detecting CRISPR-mediated methylome residues using a convolution neural network (CNN), in accordance with some embodiments. In the example of FIG. 1, before process 100 is executed, a CNN has been previously trained to a degree such that the CNN is capable of identifying a CRISPR-edited region of a genome to a predetermined level of accuracy. The CNN may have been trained, for example, using process 200 described below with respect to FIG. 2.

Prior to step 102, sequence data may be derived from various tissue samples of organisms of interest. In some embodiments, these samples may be tissue-specific or they may comprise whole embryo samples. The genomic DNA may be then extracted and purified from these tissue samples. In embodiments wherein the sequence data is whole-genome bisulfite sequencing (WGBS) data, the genomic DNA receives a bisulfite treatment that converts each unmethylated cytosine nucleotide within the DNA to a distinguishable uracil nucleotide while leaving their methylated counterparts unaffected. Thus, the detection of any remaining cytosine residues amounts to the detection of methylation at those bases.

In some embodiments, various genomic sites of interest may be enriched prior to or during sequencing using, for example, restriction enzymes or immunoprecipitation.

Following bisulfite treatment of whole genome sample extractions, next-generation DNA sequencing (NGS) is used to sequence and assemble the entire length of the genome (within which each methylated cytosine will be detected and mapped). NGS leverages massively parallel processing technology to (simultaneously) sequence redundant fragments of DNA that map to various different regions of the genome and together cover its entire length multiple times over. These sequenced fragments are then read, aligned, and assembled on the basis of their overlapping areas. The accuracy of this method improves as the number of genomic copies that are sequenced and overlapped for comparison increases. As such, depth of coverage in DNA sequencing is quantified as the amount of overlap and/or congruence that is detected during the alignment stage. For example, if a cytosine occurring at a specific genomic location is detected five (5) times (across five sequence fragments overlapping at that base), that base has a depth of five (5). Given the variability associated with genomic methylation patterns, which may vary substantially despite being sourced from the same tissue sample, methylation coverage for a given cytosine residue may be presented as the percentage of cytosines detected out of all nucleotides (cytosines+converted uracils) detected at that same location (which should also be equivalent to the depth of coverage for the given genomic location).

For example, if out of ten complete, NGS-sequenced and aligned genomic copies, five copies call the methylation of a cytosine at a particular CpG site, then the methylation rate for that particular site would be 50%. If a CRISPR-edited, genomic counterpart reported a methylation rate of 75% at that same CpG site, then the methylation difference between the baseline and edited sites would be +25%. Furthermore, if a CRISPR-edited, genomic counterpart reported a methylation rate of 25% at that same CpG site, then the methylation difference between the baseline and edited sites would be −25%. The methylome information encoded in the sequence data may be obtained by sequencing across the genome at a sufficient depth of coverage to capture all high-density of interest CpG regions.

Figure 3A:
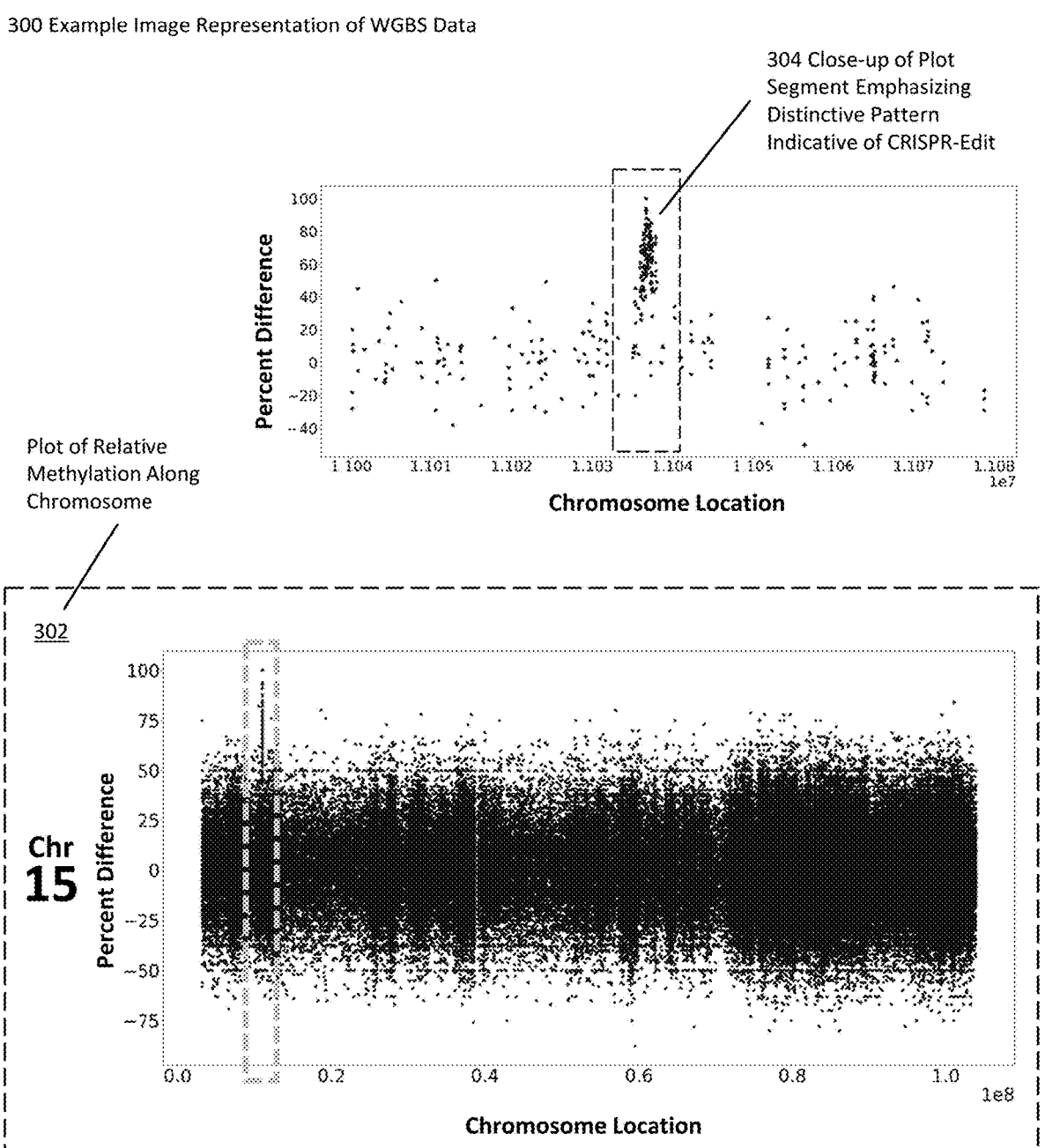
FIGS. 3A and 3B are examples of image representations of raw whole genome bisulfite sequencing (WGBS) data that is generated during the detection process and training process, in accordance with some embodiments.
Figure 3B:
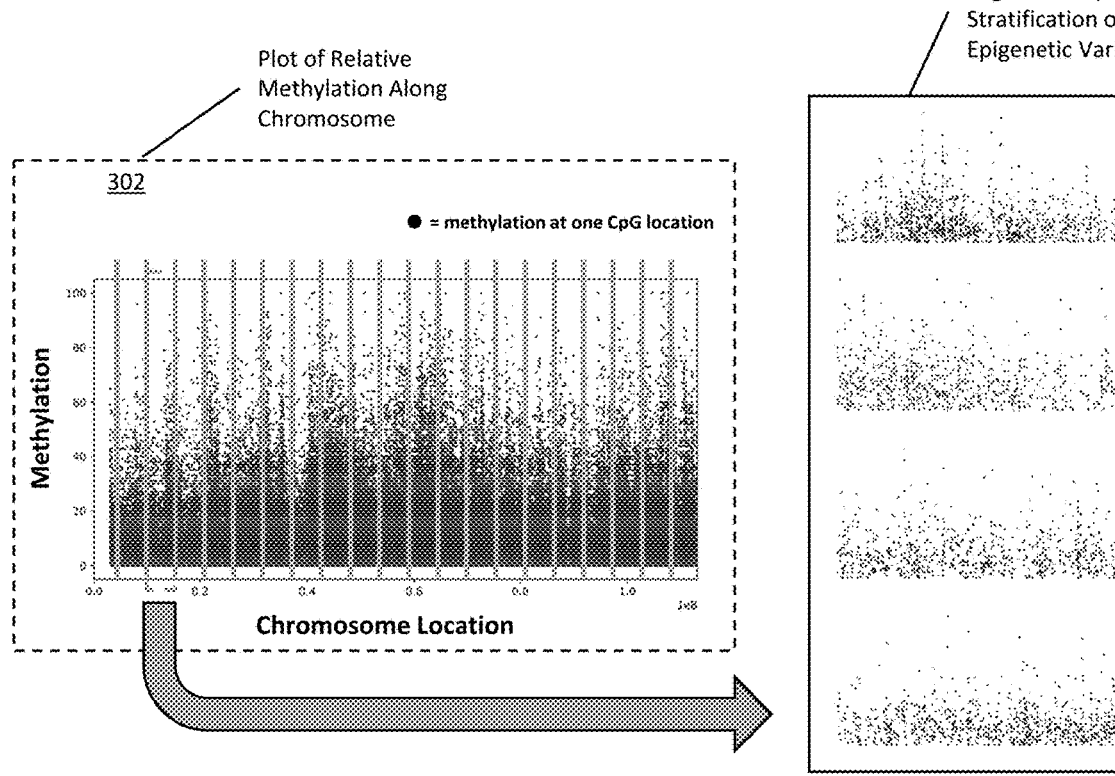
Figure 4:
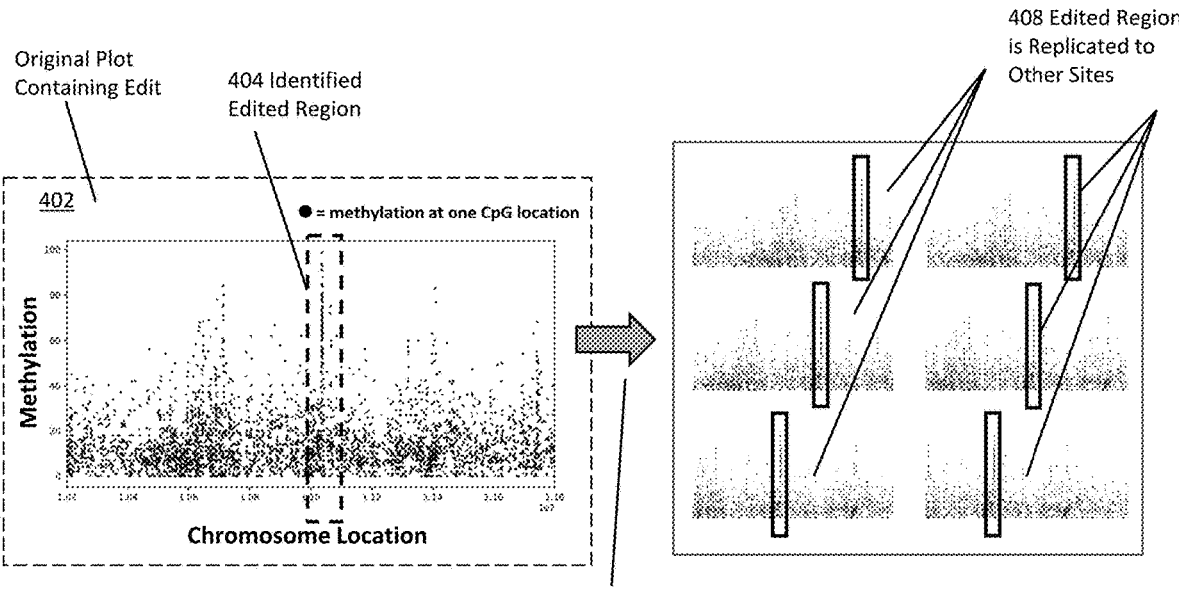
FIG. 4 shows the generation of additional image representations for training, in accordance with some embodiments.

The above approach may be used after sequencing but prior to step 102 in order to quantify the relative amounts of methylation within a genomic sequence. The subsequent data generated is later graphed during step a step 104. FIGS. 3A and 3B and FIG. 4 illustrate graphical plots that are produced during step 104: the scattering of datapoints along the Y-axis of these plots reflects the variance among methylation levels throughout a given chromosome. The generation of these plots is elaborated upon in the description of step 104 of FIG. 1.

At step 102, a processor receives sequence data of a genome suspected of having one or more CRISPR-edited methylation regions. In some embodiments, the sequence data may be received from a gene sequencing machine (e.g., via local network or the internet). Alternatively, or additionally, the sequence data may be provided by a user (e.g., using a USB drive).

At step 104, a processor generates an image representation of the sequence data. The image representation may be, for example, a plot of methylation variations with respect to a set of control data as a function of methylation location. In some embodiments, the image may be a Manhattan plot, e.g., the X axis measures variance in the methylation call for each CpG location within the sequenced epigenome while the Y axis displays the CpG location across the genomic region. As discussed below, FIGS. 3A and 3B are examples of image representations generated at this step. In some embodiments, the image representation may be a plot of the frequency of methylation calls, variance of methylation calls (within a single sample or across a plurality of samples), distribution of methylation calls, or another value indicative of methylation state at various methylation locations. In some embodiments, other types of plots may be used to illustrate the variance observed within the methylome, including scatter plots, bar plots, heatmaps, circle plots, spiral bar charts, violin plots, box plots, binned histograms, and other graphical representations of data.

The group of steps indicated by the dotted box 106 includes steps performed by a convolution neural network (CNN) detection algorithm. The CNN may be implemented on the same or different processor that performs steps 102 and/or 104. Alternatively, or additionally, the CNN may be implemented on a remote device or a remote cloud system (e.g., Google Cloud). The pixel data encoded by the image representation generated at step 104 is presented as an input to the CNN, which may incorporate one or more convolution layers, one or more pooling layers, and a scoring neuron that outputs a final value reflecting the probability that a given image contains a CRISPR-edit according to the model. In the example flow diagram of FIG. 1, the CNN applies a convolution layer in step 108 (convolving pixel data of the image representation to create feature maps), a pooling layer in step 110 (downsampling feature maps via a pooling layer), and utilizes a scoring neuron in step 112 (scoring image representation using a neural network). In some embodiments, the CNN may apply an optimal number of convolution layers (alternatively referred to as 'blocks') as determined by an Optuna parameter optimization framework described below. In these embodiments, an initial convolution layer may have a 7×7 kernel and a subsequent convolution layer may have a 3×3 kernel. In some embodiments, the pooling layer may be a global max pooling layer or a global average pooling layer, or comprise a concatenation of both.

At a step 108, the convolution layer of the CNN convolves the pixel data encoding the image representation to create feature maps (i.e., a 2 D array that which summarizes the presence and location of the detected features in the input image). Through this process the CNN extracts recurrent features and/or topographies. The features may include, for example, a plurality of lines, shapes, and colors. Each convolution layer contains a set of filters (i.e., kernels), which is a matrix of parameters that are learned through training and applied to the image input, allowing for the generation of feature maps. Specifically, these kernels iterate through the image and compute the dot product between the filter entries and the corresponding input to create feature (or activation) maps that define the output of the CNN.

At step 110 the pooling layer of the CNN downsamples the feature maps generated by the convolution process 108. The downsampling reduces the computational power requirements of the system and accounts for translation-invariance in convolutional layer features. The amount by which the data contained by a feature map is downsampled is dependent upon the values that are selected for the stride and kernel size of the pooling layer. For example, setting the stride value of the pooling layer to 2 will result in halving the size of the data during step 110. Both higher stride and higher kernel sizes result in a greater amount of downsampling to occur. The pooling operation may down sample or reduce overall dimensionality of the layer input by, for example, imputing a small set of descriptive statistics summarizing the numerical distribution of a given feature map. This process may be referred to as "flattening." Therefore, the size of the feature maps decreases throughout the network as the outputs of previous layers are taken as input to subsequent convolutional layers.

At step 112, a scoring neural network receives the compressed data (i.e., surviving activation signals) from the pooling layer and uses a rectified linear unit (ReLU) activation function to pass the activation signals through the neuron layers within the scoring neural network. A final scoring neuron then applies a sigmoid activation function to the resulting activation signals to determine a numerical score (ranging from 0 to 1) indicating the probability that the given image contains an edit (i.e., contains features that strongly correspond to the learned features indicative of a CRISPR edit). A value of 1 means the model is certain there is an edit in the input image, and 0 means there is no chance that the input image contains an edit.

At step 114, the processor uses the numerical score obtained during step 112 from the CNN to determine whether a CRISPR-scar has been detected within the plot. In some embodiments, the processor may compare the score from CNN to a predetermined threshold value (i.e., confidence score indicating the likelihood of a CRISPR edit). In some embodiments, the processor may further identify the specific methylation location of the CRISPR edit (i.e., CpG start and end positions along a chromosome), rank a gallery of predicted, anomalous detections by probability, and/or compare the relative output of multiple network models.

Figure 2:
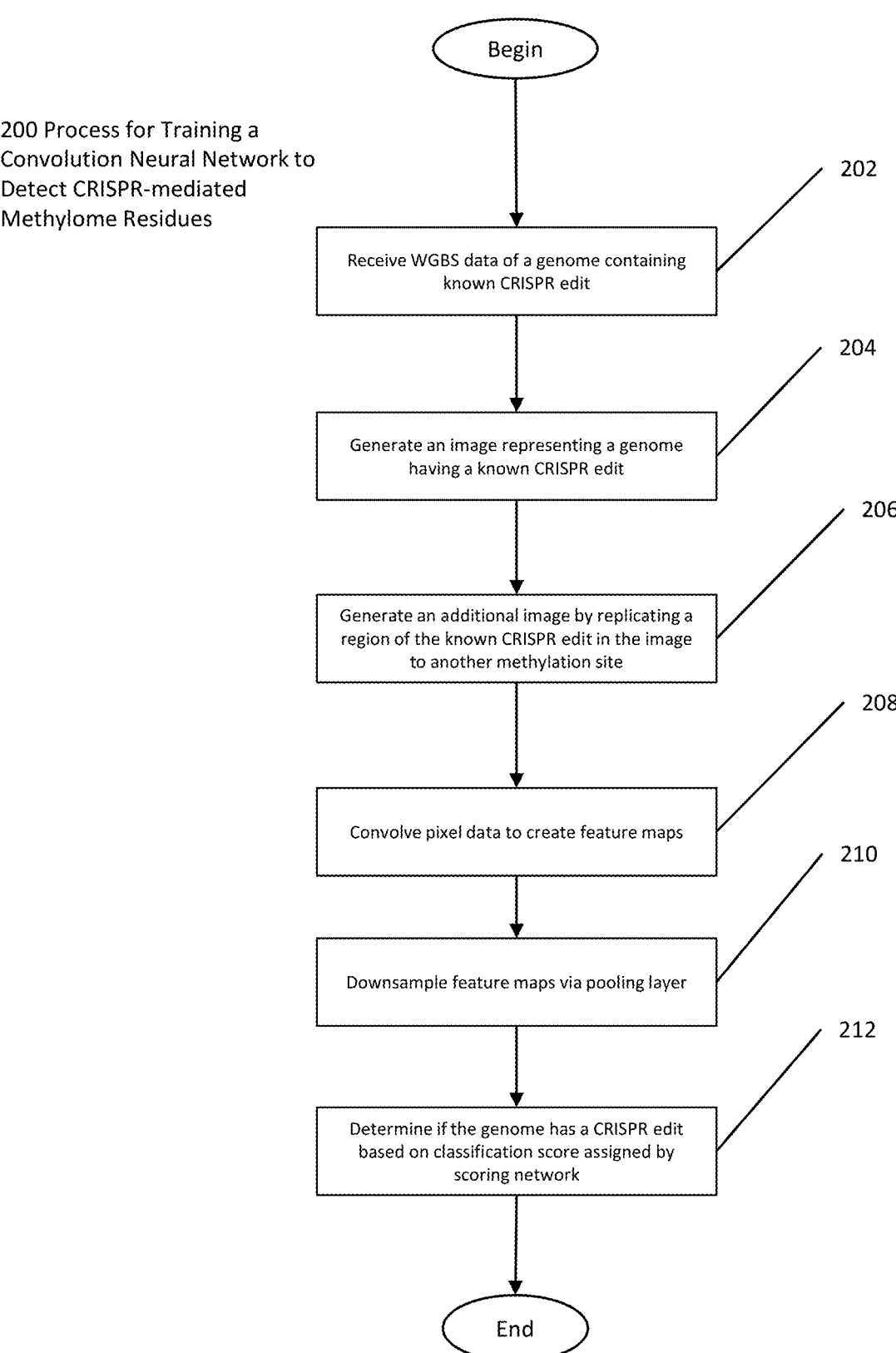
FIG. 2 is a flow diagram of a process for training the CNN used for detecting CRISPR-mediated methylome residues, in accordance with some embodiments.

FIG. 2 is a flow diagram of an example process 200 for training the CNN used for detecting CRISPR-mediated methylome residues, in accordance with some embodiments. CRISPR-scars manifest as regions of differing pixel distributions within the Manhattan plots. Process 200, which closely resembles process 100, may be used as an initial training process for the CNN prior to its utilization within process 100. Once the CNN has reached a satisfactory level of performance (i.e., is able to reliably detect CRISPR residues within new, unseen methylation datasets with a high degree of accuracy) following an extended period of training and validation, the mature, trained CNN may be considered competent to perform the group of steps 106 (and thus eligible to participate in process 100). Alternatively, or additionally, process 200 may be used to further train the CNN that has already been trained to produce results at or better than the predetermine level of accuracy. To automatically differentiate these regions from typical, scattered distribution and/or background noise, a CNN algorithm is trained to interpret distribution characteristics and features of these regions in a translationally invariant way (i.e., such that a given motif and/or class of motifs are detectable by the CNN regardless of their exact position or orientation within a genomic plot).

At step 202, a processor receives sequence data (including CpG start locations and methylation percentage data for the epigenome of a given tissue sample) of a genome that has at least one known CRISPR edit at a known methylation location. In some embodiments, the processor may also receive data indicating the methylation location of the CRISPR edit. In some embodiments, the sequence data used in step 202 may have been previously identified as having a CRISPR edit. For example, after using process 100 of FIG. 1 to determine whether sequence data of a genome has a CRISPR edit (and/or the location of such an edit), the sequence data may be fed back into the CNN as the sequence data of step 202 in process 200 thereby further training the CNN.

In some embodiments, the sequence data used in step 202 may be completely or partially derived from unedited control tissue samples. These training materials are presented to the CNN so that it learns to recognize biological noise and/or background variation in addition to unusual motifs.

At step 204, the processor generates PNG files containing images of the plots created from the received sequence data. Step 204 is analogous to step 104 of process 100. An example image generated at this step is shown in and described with respect to FIG. 3. In this embodiment, each image represents a 1-million base pair window, and methylation values are plotted at each CpG within the window. These images are generated for every chromosome in the entire genome for every control and edited sample, resulting hundreds of thousands of PNG files.

At step 206, the processor utilizes images of known CRISPR-edited samples to generate additional edited images to pass into the CNN as inputs. To generate the additional images, the processor may duplicate the image generated at step 204 and replicate a part of the duplicated image that represents a methylation region known to have a CRISPR edit to another part of the duplicated image. The edit-motif is then shifted within the image upstream and downstream of its original location, providing varied instances of the flanking regions surrounding the original training edit. Additionally, the edit-motif can be inserted into similar genomic locations occurring on entirely separate plots to provide a varied "background" against which edit-motif are detected. The process for generating additional images is referred to as "data augmentation" and is described below with respect to FIG. 4.

Subsequently, pixel data of the image generated at step 204 and the pixel data of the additional images generated at step 206 are provided collectively as input to the CNN used for detection in FIG. 1. At steps 208, 210, and 212 of FIG. 2, the CNN trains its internal algorithm by adjusting and optimizing its network of synaptic weights to recognize input images of methylation regions that are intrinsically similar to methylation disturbances of known CRISPR-edited regions.

At step 208, the convolution layer of the CNN convolves matrices (i.e., kernels) to define sampled regions upon which a training iteration (i.e., epoch) takes place. For every training iteration, multiple convolutions are downsampled into a pooling layer at step 210 to learn and preserve the feature vector representation of the data.

Within the given convolution layer presented in step 208, the overall plot image is separated into an array of kernels, which has the effect of dividing the regions of pixels that make up the overall methylation plot image into discrete regions. Each pixel that is part of a plot point is assigned a uniform numerical value. The convolution process proceeds by computing a weighted sum of the values (i.e., frequency of pixels) within a particular kernel to create a feature map. Then, the sampling frame shifts (according to the kernel size stride) so that the kernel is centered around a new pixel, and the subsequent area is resampled, creating a new feature map. The relocated kernel will overlap with some (but not all) of the pixels bounded by its previous position. Therefore, convolution inherently oversamples data as it revolves around a given pixel or origin point.

In step 210, a pooling layer downsamples feature maps (i.e., inputs from the convolution layer 208) to account for overlapping data (and to reduce computational power requirements). This is performed by calculating a set of summary statistics for each convolution between the kernel and an image, including: calculating the average value for each matrix in a given feature map, calculating the maximum value for each matrix within the a given feature map, calculating the global average value for each entire feature map, and calculating the global maximum value for each entire feature map.

Pooling layers from step 210 take input from convolutional layers and flatten them, reducing the dimensionality of the layer input. Generally, the size of the feature maps decreases as movement through the network progresses and the outputs of previous convolutional layers are taken as input to subsequent convolutional layers.

The resulting output from the pooling step 210 presents the summary statistics to a scoring network at step 212, which contains dense nodes with parameters that are learned through training. The Sigmoid scoring function outputs a value between 0 and 1 so as to indicate the probability that a given CpG site within the current plot image under evaluation contains an edit.

In some embodiments, the CNN process utilizes an Optuna parameter optimization framework, which allows for systematic and automatic optimization of training variables, which in turn, reduces the down-time of training cycles. Hyperparameters such as the number of convolution blocks (2, 3, or 4), kernel size (3, 5, 7, 9, or 11), number of filters (16, 32, 48, or 64), stride (1, 2, or 3), number of dense nodes (128, 256, 512, or 1024), learning rate (0.0001, 0.001, 0.01, or 0.05), choice of optimizer (RMSProp, Adam, or SGD) may be selected.

These hyperparameters are optimized through several rounds of training initializing with random combinations of hyperparameter values as the starting point for future training rounds. The best model in terms of training accuracy, validation accuracy, and loss is used for model prediction.

FIG. 3 illustrates an example image representation of raw WGBS data that is generated at step 104 of process 100 and step 204 of process 200, in accordance with some embodiments. FIG. 3A and FIG. 3B each display alternate presentations of a sample plot of methylation data, accompanied by close ups that emphasize a distinctive pattern indicative of a CRISPR-edit and stratification of epigenetic variance, respectively. The region indicated by 304 is illustrative of a distinctive pattern (i.e., methylation footprint) that indicates the occurrence of a CRISPR-edit. Plot 306 is a close up of methylation data along a narrow chromosomal region, indicating the variable degree of resolution to which a CNN may be trained. In this example, the image is of a Manhattan plot used to visually convey the percentage of variance in methylation calls observed among CpGs relative to their unmodified, control counterparts. Thus, each individual datapoint indicates the methylation percentage difference for its respective CpG genomic location. In some embodiments, a threshold of statistical significance or read depth may be selected prior to plot generation so as to filter the sample set and reduce potential overfitting of the dataset by the model.

In some embodiments, higher resolution and/or more detailed images may be used to make it easier for models to determine key differences between edits and non-edits, ensuring that features indicative of CRISPR-edits are captured within the overall image that contains them.

FIG. 4 are annotations of additional image representations for training and correspond to step 204 of process 200, in accordance with some embodiments. In FIG. 4, the chromosomal plot 402 (an image comprising 1.5 million base pairs) is sliced into sections of tunable size denoted by 404. Regions of high pixel density and/or abnormal distribution in particular may be attached or implanted within different regions of its native plot or integrated into other plots to proliferate the amount of training images that teach the features of CRISPR-edits. The family of data augmented images 408 (which may actually comprise thousands of augmented views) was created by variably shifting (an embodiment of 406) the 404 region along the X axis of 402.

Whether to expand a limited pool of samples on which to train or to combat an overfitted model, synthetic (i.e., contrived) datasets comprising slightly modified copies of preexisting data can be used to supplement a CNN. The number of samples can be augmented by performing certain minimal transformations 406 on the original data. For example, when training a neural network in image recognition, a set of images can be processed by having every image (or a portion of a given image) duplicated, translated, mirrored, and/or rotated through a plurality of rotation angles and a plurality of translation distances and directions. These approaches train the algorithm that genomic edits can occur in any region and/or orientation of the plotted sector.

Another augmentation approach (not shown in FIG. 4), nests the edited data in randomized regions of the genome with similar CpG distribution as the edited region, providing illustrations of edits occurring in other locations across the genome.

A CNN paradigm is selected over other network architectures for its ability to rapidly extract features within visual representations (e.g., graphical plots, mappings, etc.) of methylation pattern distributions across a given chromosome in an unsupervised setting, wherein region-of-interest segmentation output images are computed to remove noise and/or artifacts, and directed to classify based on extracted features. In some embodiments, this could be combined with additional statistical or computational methods in order to imbue an ensemble of detection strategies with a CNN's advantageous characteristics. In particular, a CNN may represent an ideal complement to an LSTM approach, which relies upon a slower, supervised training regime. Inversely, in other embodiments, the CNN module may be preferentially trained in a supervised fashion with feature-labeled region of interest training images, diagnostic training data, or combinations thereof, to extract features from the regions of interest.

In some embodiments, a plurality of plot-types may contribute to a training data set for the CNN, with the different representations emphasizing one or more unique image characteristics (e.g., boundaries, densities, etc.).

Figure 5:
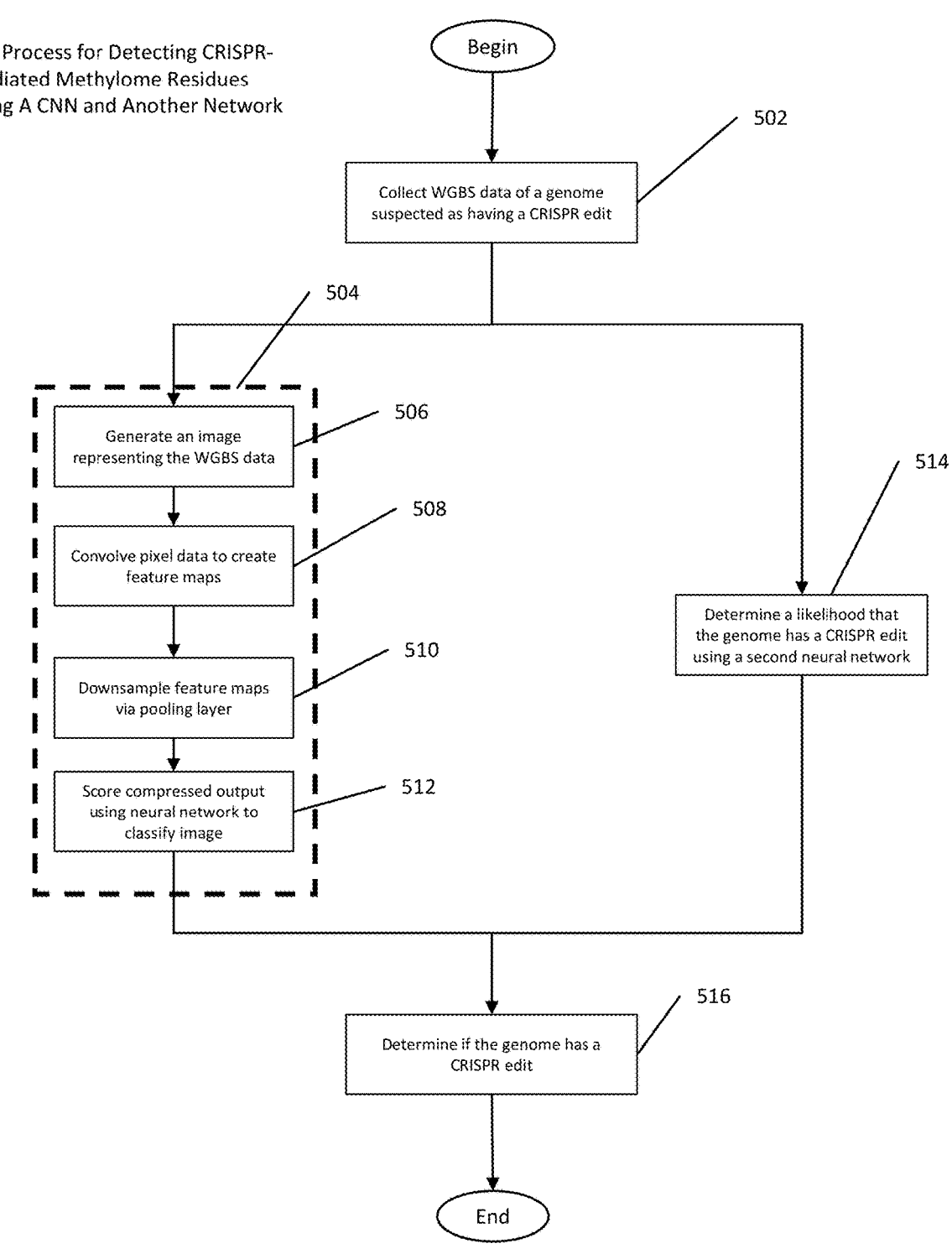
FIG. 5 is a flow diagram of another process for detecting CRISPR-mediated methylome residues using a trained CNN and a second neural network, in accordance with some embodiments.

FIG. 5 is a flow diagram of another process 500 for detecting CRISPR-mediated methylome residues using a trained CNN 504 and a second neural network, in accordance with some embodiments. Steps 502-512 are similar to steps 102-112 of FIG. 1.

At step 514, the second neural network may determine a likelihood that the genome has a CRISPR edit. In some embodiments, the second neural network may be a long short-term memory (LSTM) autoencoder that is specialized to identify patterns within sequences of data. An LSTM network is employed to recognize sequences of unedited epigenetic data by making sequence predictions using its trained algorithm and measuring error between the predicted output and the original input. If the error surpasses a certain threshold, then a CRISPR-edited region is suspected, and statistical tests are then employed to verify whether a positive detection was made.

In some embodiments, step 514 may be performed concurrently and/or in parallel with the CNN 504. Other architectures and/or organizations of the detection method may instead arrange one or more networks to feed evaluation data into the other in a series.

At step 516, a processor may determine if the genome has a CRISPR edit based on (1) a final classification from the CNN 506 and (2) an output from a second neural network indicative of a likelihood that the genome has a CRISPR edit. In some embodiments, the processor may determine if the genome has a CRISPR edit by calculating a composite score based on the score from the CNN and the output from a second neural network and comparing the composite score to a predetermined threshold value.

Figure 6:
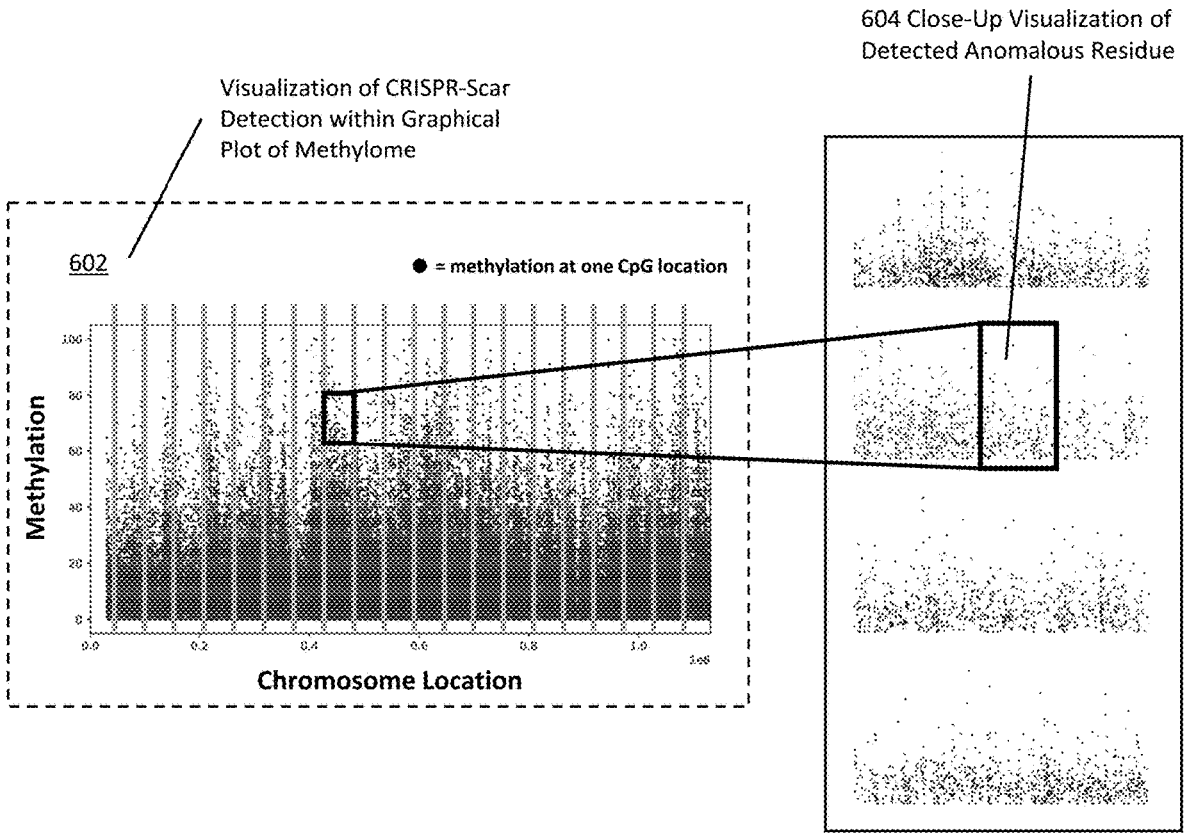
FIG. 6 illustrates an example of a user interface for indicating that a genome contains one or more methylation region that has been CRISPR-edited.

FIG. 6 illustrates an example user interface for indicating that a genome contains one or more methylation region that has been CRISPR edited. As shown in FIG. 6, a visualization of CRISPR-scar sites within the overall graphical plot 602 of the methylome conveys the exact locations of the detections by the model. These regions of interest can be magnified to provide greater resolution and/or detail of an anomalous residue in 604. In addition to identification, other embodiments may rank the likelihoods that detected areas contain CRISPR-scars.

FIG. 7 illustrates an example of a table 700 used to compare and competitively select for combinations of CNN hyperparameters that minimize the loss of their corresponding models. A loss function is used by CNNs to compare the target and predicted output values of a given model. The calculated loss measures how well the neural network models the training data (i.e., how accurately known CRISPR-edited sites are identified by the CNN). This process is analogous to statistical residual analysis, which measures the distance of the actual values output by a given function (i.e., training data) from a regression line (i.e., values predicted by a model). In some embodiments, mean squared error (MSE) or mean absolute error (MAE) may be utilized by a CNN to measure the loss (i.e., distance) between its target and predicted outputs. During training, the goal of the CNN is to minimize this loss between the predicted and target outputs. Once a given model has produced an output, this predicted output is compared against the given target output in a process called backpropagation—the hyperparameters of the model are then adjusted so that it outputs a result closer to the target output (i.e., detects CRISPR-edited sites with improved accuracy) in successive training cycles.

CNN hyperparameters 702 (e.g., learning rate, optimizer, etc.) are at first initialized using random combinations of hyperparameter values and then optimized through several rounds of training by iteratively taking the best performing combinations of hyperparameter values 704 and repurposing them as starting points for future training rounds. The models ranked best in terms of training accuracy, validation accuracy, and loss minimization as reflected by the 706 columns are used for model prediction. The loss function measures the inaccuracy of the model following each iteration of testing, which informs the model by how much to adjust its synaptic weights so as to reduce net loss in the following round of training. In this embodiment, binary cross-entropy is used as the loss function. Table 700 (which is sorted in the descending order of loss) shows hyperparameters including kernel size of all incorporated convolutional blocks, the number of convolution blocks, and the number of filters favoring production of the lowest loss. Specifically, the small feature size of CRISPR-edit methylation footprints relative to the overall size of the image may create a preference for smaller kernels. Additionally, no models containing less than three convolution blocks occupy the top five positions of table 700 (indicating that these datasets perform better with deeper models), while a relatively low number of filters is also correlated with lower loss. Accordingly, in some embodiments, to achieve a low loss, the CNN may include a convolution layer with a kernel size that does not exceed 5×5 (i.e., 1×1, 2×2, 3×3, 4×4, or 5×5), a minimum of three convolution blocks, and under 32 filters.

FIG. 8 illustrates an example of a table used to rank the relative likelihoods that a CRISPR-edit exists at various CpG sites 802 by taking into account the predictions made by multiple CNN models 804 and calculating an overall mean probability. Probabilities ranking in the top positions of the table have been verified to align closely with known CRISPR-edited sites occurring at these CpG locations, while low-likelihoods of detection appearing at the bottom of the table were similarly validated by the absence of any known CRISPR-edits at those locations. Additionally, table 800 demonstrates the integrative approach of pooling the probabilities for detection across several models. In some embodiments, this may serve as a method of averaging out biases and/or neutralizing failed predictions by individual models. Alternatively, table 800 may be reflective of the model selection and/or optimization process by revealing underperforming models that deviate inaccurately from consensus predictions and are thus eliminated from further use.

While illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed routines may be modified in any manner, including by reordering steps and/or inserting or deleting steps. It is intended, therefore, that the specification and examples be considered as illustrative only, with a true scope and spirit being indicated by the following claims and their full scope of equivalents.

We claim:

1. A system for detecting a CRISPR-edited genome, comprising:

One or more processors configured to:

receive sequence data of a genome;

generate an image representation of the sequenced data, the image being a plot of methylation variations as a function of methylation locations in the genome;

provide the generated image representation to a convoluted neural network (CNN), wherein:

the CNN was trained using: (1) a training image representing sequenced data of a CRISPR-edited genome, and (2) an additional training image generated based on the training image, and the additional training image is generated by (1) duplicating the training image, and (2) replicating a part of the training image corresponding to a CRISPR-edited methylation region of the CRISPR-edited genome to a part of the duplicated training image corresponding to a different methylation region;

generate, using the CNN, a score indicative of a probability that the genome was CRISPR-edited; and determine, based on the score, whether the genome contains a CRISPR-edited methylation region.

2. The system of claim 1, wherein the sequenced data is whole-genome bisulfite sequencing (WGBS) data.

3. The system of claim 1, wherein the image is a Manhattan plot.

4. The system of claim 1, wherein the CNN includes convolution layers and a pooling layer.

5. The system of claim 1, wherein, after determining that the genome contains a CRISPR-edited methylation site, uses the image representation of the sequenced data to further train the CNN.

6. The system of claim 1, wherein the determining includes determining a methylation location of the CRISPR edit.

7. The system of claim 1, wherein one or more processors are further configured to determine, using an LSTM, whether the genome likely contains a CRISPR-edited methylation site, wherein the determining includes weighing the generated score and results from the LSTM to determine whether the genome contains a CRISPR edit.

8. A method for detecting a CRISPR-edited genome, comprising:

receiving sequence data of a genome;

generating an image representation of the sequenced data, the image being a plot of methylation variations as a function of methylation locations in the genome;

providing the generated image representation to a convoluted neural network (CNN), wherein:

the CNN was trained using: (1) a training image representing sequenced data of a CRISPR-edited genome, and (2) an additional training image generated based on the training image, and the additional training image is generated by (1) duplicating the training image, and (2) replicating a part of the training image corresponding to a CRISPR-edited methylation region of the CRISPR-edited genome to a part of the duplicated training image corresponding to a different methylation region;

generating, using the CNN, a score indicative of a probability that the genome was CRISPR-edited; and determining, based on the score, whether the genome contains a CRISPR-edited methylation region.

9. The method of claim 8, wherein the sequenced data is whole-genome bisulfite sequencing (WGBS) data.

10. The method of claim 8, wherein the image is a Manhattan plot.

11. The method of claim 8, wherein the CNN includes convolution layers and a pooling layer.

12. The method of claim 8, wherein, after determining that the genome contains a CRISPR-edited methylation site, uses the image representation of the sequenced data to further train the CNN.

13. The method of claim 8, wherein the determining includes determining a methylation location of the CRISPR edit.

14. The method of claim 8, further comprising determining, using an LSTM, whether the genome likely contains a CRISPR-edited methylation site, wherein the determining includes weighing the generated score and results from the LSTM to determine whether the genome contains a CRISPR edit.

15. A non-transitory computer-readable storage medium storing instructions that when executed by a computer cause the computer to perform a method for detecting a CRISPR-edited genome, the method comprising:

receiving sequence data of a genome;

generating an image representation of the sequenced data, the image being a plot of methylation variations as a function of methylation locations in the genome;

providing the generated image representation to a convoluted neural network (CNN), wherein:

the CNN was trained using: (1) a training image representing sequenced data of a CRISPR-edited genome, and (2) an additional training image generated based on the training image, and the additional training image is generated by (1) duplicating the training image, and (2) replicating a part of the training image corresponding to a CRISPR-edited methylation region of the CRISPR-edited genome to a part of the duplicated training image corresponding to a different methylation region;

generating, using the CNN, a score indicative of a probability that the genome was CRISPR-edited; and determining, based on the score, whether the genome contains a CRISPR-edited methylation region.

16. The non-transitory computer-readable storage medium according to claim 15, wherein the sequenced data is whole-genome bisulfite sequencing (WGBS) data.

17. The non-transitory computer-readable storage medium according to claim 15, wherein the image is a Manhattan plot.

18. The non-transitory computer-readable storage medium according to claim 15, wherein the CNN includes convolution layers and a pooling layer.

19. The non-transitory computer-readable storage medium according to claim 15, wherein, after determining that the genome contains a CRISPR-edited methylation site, uses the image representation of the sequenced data to further train the CNN.

20. The non-transitory computer-readable storage medium according to claim 15, wherein the determining includes determining a methylation location of the CRISPR edit.

* * * * *